United States Patent [19]

Uenoyama et al.

[11] Patent Number: 5,382,346
[45] Date of Patent: Jan. 17, 1995

[54] BIOSENSOR AND METHOD OF QUANTITATIVE ANALYSIS USING THE SAME

[75] Inventors: Harumi Uenoyama, Takatsuki; Hisashi Okuda, Uji, both of Japan

[73] Assignee: Kyoto Daiichi Kagaku Co., Ltd., Kyoto, Japan

[21] Appl. No.: 138,263

[22] Filed: Oct. 20, 1993

Related U.S. Application Data

[63] Continuation of Ser. No. 883,367, May 15, 1992, Pat. No. 5,332,479.

[30] Foreign Application Priority Data

May 17, 1991 [JP] Japan ................. 3-113030

[51] Int. Cl.$^6$ .................................... G01N 27/26
[52] U.S. Cl. ........................... 204/403; 204/415; 204/418; 435/817
[58] Field of Search .............. 204/403, 418, 415; 435/817

[56] References Cited

U.S. PATENT DOCUMENTS

| | | | |
|---|---|---|---|
| 3,539,455 | 11/1970 | Clark, Jr. | 204/415 |
| 3,707,455 | 12/1972 | Derr et al. | 204/415 |
| 3,979,274 | 9/1976 | Newman | 204/415 |
| 4,240,889 | 12/1980 | Yoda et al. | 204/415 |
| 4,340,448 | 7/1982 | Schiller et al. | 204/153.12 |
| 4,431,507 | 2/1984 | Nankai et al. | 204/403 |
| 5,120,420 | 6/1992 | Nankai et al. | 204/403 |

FOREIGN PATENT DOCUMENTS

| | | |
|---|---|---|
| 0304947 | 1/1989 | European Pat. Off. . |
| 0359831 | 3/1990 | European Pat. Off. . |
| 2643150 | 8/1990 | France . |
| 57-118152 | 7/1982 | Japan . |
| 57-211054 | 12/1982 | Japan . |
| 57-211542 | 12/1982 | Japan . |
| 58-5642 | 1/1983 | Japan . |
| 58-5643 | 1/1983 | Japan . |
| 58-17427 | 4/1983 | Japan . |
| 58-85148 | 5/1983 | Japan . |
| 58-85149 | 5/1983 | Japan . |
| 58-146847 | 9/1983 | Japan . |
| 1-253648 | 10/1989 | Japan . |

OTHER PUBLICATIONS

"Electrochemical On-Line Elimination of Electroactive Interferents for Flow-Type Biosensor System," by Y. Okawa et al., pp. 97–100, 11th Chem. Symposium.
Miyahara et al., *Sensors and Actuators*, 7, (1985), "Integrated Enzyme FETS for Simultaneous Detections of Urea and Glucose," pp. 1–10.

*Primary Examiner*—John Niebling
*Assistant Examiner*—Bruce F. Bell
*Attorney, Agent, or Firm*—Birch, Stewart, Kolasch & Birch

[57] ABSTRACT

A biosensor which electrochemically detects a material which relates to a reaction of a specific compound in a liquid sample with a biologically active substance or its related substance, in which the biologically active material or an optionally used mediator is placed at a part which is remote from a position of an electrode which acts as electrochemical detector means, and optionally the biological active material or the mediator is covered with a polymer layer.

7 Claims, 4 Drawing Sheets

BIOSENSOR AND METHOD OF QUANTITATIVE ANALYSIS USING THE SAME

This application is a continuation of copending application Ser. No. 07/883,367, filed on May 15, 1992, now U.S. Pat. No. 5,332,479, the entire contents of which are hereby incorporated by reference.

BACKGROUND OF THE INVENTION

1. Field of the Invention

The present invention relates to a biosensor and a method of quantitative analysis of a material which relates to a reaction of a specific compound in a liquid sample with a biologically active substance such as an enzyme.

2. Description of the Related Art

When a biological liquid sample such as blood is analyzed using a biosensor which comprises electrochemical detecting means, a reducing compound such as ascorbic acid or uric acid which is present in the sample has an electrochemical or chemical interference on the analysis, which is always a problem in the analysis.

Hitherto, various measures to remove or suppress such interference have been proposed in patent specifications and literatures. They are summarized as follows:

(1) Use of an Interference-removing Membrane

U.S. Pat. Nos. 3,979,274 and 4,240,889, Japanese Patent Kokai Publication Nos. 211542/1982 and 5643/1983, etc.

(2) Electrode Oxidation

U.S. Pat. No. 4,431,507, Japanese Patent Kokai Publication Nos. 118152/1982, 211054/1982, 5642/1983, 85148/1983, 85149/1983 and 146847/1983, The 11th Chemical Sensor Symposium, Okawa et al, 24. "Electrochemical On-Line Elimination of Electroactive Interference for Flow-Type Biosensor System", etc.

(3) Use of Plural Working Electrodes

U.S. Pat. No. 3,539,455, Japanese Patent Kokai Publication Nos. 146847/1983 and 253648/1989, Miyahara et al, Sensor and Actuators, 7, 1 (1985), etc.

(4) Addition of an Enzyme for Oxidizing an Interfering Substances

Japanese Patent Publication No. 17427/1983

(5) Double Potential Step Method

The 58th Spring Annual Meeting of the Japan Chemical Society, 4IG06, Matsuura et al, "Measurement of Hydrogen Peroxide with A Micro Carbon Fiber Electrode".

However, each of the above measures has its own drawbacks as follows:

(1) Use of an Interference-removing Membrane

In this method, an electrode which is an electrochemically detecting device is covered with a selectively permeable membrane, whereby a substance to be analyzed permeates the membrane while concomitant interfering substances do not. This method can be employed when a substance having a very low molecular weight such as oxygen molecules or hydrogen peroxide is used as an electrochemically reactive substance. But, when a mediator for electric charges such as potassium ferricyanide or ferrocene is used, this method cannot be applied since the concomitant interfering substance and the mediator cannot be distinguished according to their sizes. Further, this method cannot be a remedy for an oxidation-reduction reaction between the concomitant substance and the mediator which takes place outside the interference-removing membrane, namely in the sample liquid. In addition, the membrane may decrease a sensitivity and a response of the electrode and a degree of such deterioration depends on a thickness of the membrane so that a difference between individual sensors is enlarged.

(2) Electrode Oxidation

This method requires an additional electrode system for anodizing the concomitant interfering substance in the sample (an electrolytic electrode system) in addition to an electrode system for measuring an object substance (a measuring electrode system). When the sample is supplied to a measuring system, the interfering substance is anodized by the electrolytic electrode system before it reaches an enzyme reaction system or the measuring electrode system.

Since this method essentially requires the electrolytic electrode system in addition to the measuring electrode system, and two electrode systems and the reaction system of the biologically active substance such as an enzyme are spacially separated, the sensor has a complicated structure. To increase an electrolytic efficiency of the interfering substance, a surface area of the electrolytic electrode is increased, or the sample liquid is intentionally stirred or flowed. However, the structure of the sensor is complicated and enlarged, or the response is decreased. This method may not be suitable for a disposable sensor.

The increase of the electrolytic efficiency of the interfering substance is contrary to the reduction of the measuring time and the increase of the response. To satisfy both requirements, a very thin integrated porous electrode system is proposed. But, since such thin electrode is weak and unstable, it requires reinforcement of the structure so that it is difficult to supply a simple and cheap sensor.

Since the sensor as a whole has the electrolytic electrode system in addition to the measuring electrode system, electric circuits and a measuring software become complicated and expensive.

(3) Use of Plural Working Electrodes

In this method, an electrode system for measuring the interfering substance present in the sample is used in addition to the measuring electrode system. When the sample is supplied, the measuring electrode system measures signals from both the object substance and the interfering substance while the electrode system for measuring the interfering substance measures only the signal from the interfering substance. Then, a difference between these two measured value is calculated to give a concentration of the object substance to be measured.

This method essentially requires the electrode system for measuring the interfering substance. Since there is a possibility that a reaction product or reaction products produced by the measuring electrode system may have some influence on the electrode system for measuring the interfering substance, these two electrode systems should be spacially separated with a sufficient distance. This results in enlargement and a more complicated structure of the whole sensor. Since two or more electrode systems are used, two or more electric circuits for amplifying detected currents are necessary.

Further, measuring sensitivities for the object substance measurement and the interfering substance measurement should be matched, but such matching of the sensitivities is very difficult practically. In the case of a repetitive use sensor, the sensitivities of the electrode systems for measuring the interfering substance may be calibrated, but such calibration is impossible for the disposable sensor.

(4) Addition of an Enzyme for Oxidizing an Interfering Substance

In this method, the interfering substance such as ascorbic acid or uric acid is oxidized with a respective oxidase before it participates in the electrode reaction or the oxidation-reduction reaction with the substance to be measured. Since a highly specific enzyme is used to remove the interfering substance in this method, plural enzymes should be used when plural interfering substances are present in the sample. This leads to the increase of a production cost of the biosensor. The preoxidation of the interfering substance is essential, and it is necessary to prevent interference of the measurement of the object substance caused by a product from oxidation of the interfering substance. Therefore, the sensor has a complicated structure inevitably. In addition, the interfering substance is removed through a conversion by the oxidation to a material which cannot be measured. This means that some information, which may be valuable if measured, is discarded.

(5) Double Potential Step Method

When a natural potential ($E_{02}$) of the measuring electrode against the object substance to be measured and a natural potential ($E_{01}$) against the interfering substance are different (assuming $E_{01} < E_{02}$), the concentration of the interfering substance is measured at a potential $E_1$ which satisfies $E_{01} < E_1 < E_{02}$, while a total concentration of the object substance and the interfering substance is measured at a potential $E_2$ which is larger than $E_{02}$ ($E_{02} < E_2$), and then a difference between $E_1$ and $E_2$ is calculated to obtain the concentration of the object substance.

According to the measuring principle of this method, if the natural potential $E_{02}$ against the object substance and the natural potential $E_{01}$ against the interfering substance are not sufficiently different, the concentration of the object substance and the total concentration of the object substance and the interfering substance cannot be separated and measured. When the object substance to be measured is hydrogen peroxide, the above potential relationship can be often established. Depending on an electrode substance or a surface condition of the electrode, $E_{01}$ and $E_{02}$ are very close to each other or sometimes $E_{01}$ exceeds $E_{02}$.

To achieve stability or expansion of a linear range of the biosensor, the mediator is often used. In such case, the electric charges are transferred with the mediator between the electrode and the object substance to be measured or the interfering substance, $E_{01}$ and $E_{02}$ are equal. Therefore, the double potential step method cannot be used.

SUMMARY OF THE INVENTION

One object of the present invention is to provide a biosensor which can isolate a signal from an object substance to be measured from a signal from an interfering substance.

Another object of the present invention is to provide a method of quantitative analysis of a material which relates to a reaction of a specific compound in a liquid sample with a biologically active substance such as an enzyme.

According to a first aspect of the present invention, there is provided a biosensor which electrochemically detects a material which relates to a reaction of a specific compound in a liquid sample with a biologically active substance or its related substance (hereinafter referred to as "biologically active material"), wherein the biologically active material or an optionally used mediator is placed at a part which is remote from a position of an electrode which acts as electrochemical detector means, and optionally the biological active material or the mediator is covered with a polymer layer.

According to a second aspect of the present invention, there is provided a method of quantitative analysis of a material which relates to a reaction of a specific compound in a liquid sample with the biologically active material, comprising reading at least two electrochemical signals from the liquid sample, which are an electrochemical signal at the supply of the sample relating to an electrochemically active substance present in the sample but not to a biologically active material and an electrochemical signal after a sufficient time from the supply of the sample relating to both the biologically active material and the electrochemically active substance present in the sample and operating both signals, whereby the substance which specifically reacts with the biologically active material and the electrochemically active material present in the sample are separated and quantitatively analyzed.

DETAILED DESCRIPTION OF THE INVENTION

Figure 1:
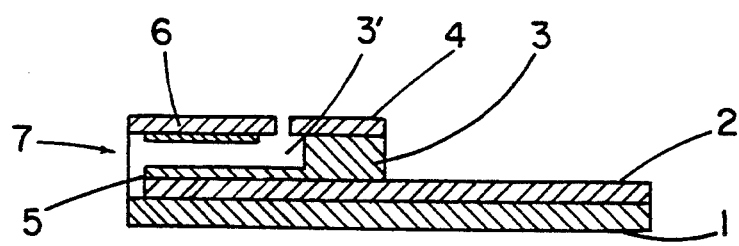
FIG. 1 is a schematic cross section of an example of the biosensor according to the present invention.

In the present invention, the biologically active material includes:

1. Substrates of oxidoreductases, for example, lactic acid, glucose, uric acid, piruvic acid, cholesterol, and the like.
2. Oxidoreductases, for example, lactase dehydrogenase, isocitrate dehydrogenase, glutamic dehydrogenase, glucose 6-phosphate dehydrogenase, and the like.
3. Substances which finally perform an oxidation-reduction reaction utilizing a reaction of a substrate or an enzyme, for example, triglyceride, phospholipid, glutamic-oxaloacetic transaminace (GOT), glutamic-pyruvic transaminace (GPT), creatine phosphokinase (CPK), and the like.
4. Substances measured by utilizing an antigen-antibody reaction, for example, immunoglobulins, hormones (e.g. $T_3$, $T_4$, etc.), and the like.

In the present invention, the wording "placing the biologically active material" intends to mean that the biologically active material is present at a specific part of the biosensor in a state that the biologically active material can react with the specific substance to be analyzed in the sample. The wording "placing the mediator" intends to mean that the mediator is present at a specific part of the biosensor in a state that the mediator can be dissolved in the liquid sample. A form of the biologically active material or the mediator is not limited. For example, a solution of the biologically active material is applied on the specific part of the biosensor and dried to place the biologically active material as a residue at the specific part of the biosensor. The solution of the biologically active material is impregnated in an absorbing material such as a filter paper or a piece of cloth and then dried, and the absorbing material carrying the biologically active material is set at the specific part of the biosensor. Further, some of the biologically active materials may be set at the specific part of the biosensor with a cross-linking agent such as glutaraldehyde or disuccinimidyl suberate. The biologically active material may be absorbed on the material of the biosensor substrate using an absorptivity therebetween.

When the biosensor utilizes the mediator, on the measuring electrode, the mediator is placed but no biologically active material is provided. The mediator may be mixed with an hydrophitic polymer and then provided.

The biologically active material is placed together with at least the mediator at the specific part of the biosensor which is sufficiently remote from the measuring electrode. The distance between the measuring electrode and the specific part where the biologically active material is placed is determined such that, in a very short time in which the mediator on the measuring electrode is dissolved in the sample after the sample is supplied and the signal due to the electrode reaction is read (for example, 0 to several seconds, e.g. 5 or 6 seconds), a mediator which is generated by the reaction between the object substance in the sample and the biologically active material does not diffuse and reach the measuring electrode.

In the case of the biosensor using no mediator such as a biosensor using a hydrogen peroxide electrode, preferably any material is not provided on the measuring electrode. To facilitate and smoothen the introduction of the sample, the hydrophilic polymer and the like may be provided on the electrode. The biologically active material is placed at the specific part of the biosensor which is sufficiently remote from the measuring electrode. The distance between the measuring electrode and the specific part where the biologically active material is placed is determined such that, in a very short time in which, after the supply of the sample, the signal generated by the direct electrode reaction of the interfering substance in the sample is read (for example, 0 to several seconds, e.g. 5 or 6 seconds), a material such as hydrogen peroxide which is generated by the reaction between the object substance in the sample and the biologically active material does not diffuse and reach the measuring electrode.

To adjust or prolong the time in which the mediator or the material such as hydrogen peroxide that diffuses from the specific part apart from the measuring electrode reaches the measuring electrode, an amount of the hydrophilic polymer to be combined with a layer of the biologically active material may be increased. Alternatively, the biologically active material layer may be covered with a layer of the hydrophilic polymer.

In the quantitative analysis method of the present invention, when or immediately after the sample is supplied (in general, within several seconds, e.g. 5 or 6 seconds), a first electric current is measured, and then after a sufficient time from the supply of the sample (in general, several ten seconds, e.g. 50 or 60 seconds), a second electric current is measured. A first measured value of the electric current is a current before the produced material of the reaction between the object substance to be measured and the biologically active material reaches the measuring electrode. With this first current, a concentration of the concomitant interfering substance(s) can be determined. A second measured value of the electric current is a current caused by the interfering substance(s) and the produced material of the reaction between the object substance and the biologically active material. With the second current, a total concentration of the concomitant interfering substance(s) and the produced material can be determined. Therefore, a difference between the total concentration determined from the second current and the concentration determined from the first current is a concentration of the object substance to be measured. Timings for measuring the first and second currents should be suitable for measuring the current attributed to the interfering substance(s) and the current attributed to both the interfering substance(s) and the produced material. Therefore, the timings for measuring the currents are not limited to the above exemplified general periods.

PREFERRED EMBODIMENTS OF THE INVENTION

The present invention will be explained in detail by following Examples, which do not limit the scope of the present invention.

EXAMPLE 1

A schematic cross section of a produced two-electrode type analysis biosensor according to the present invention is shown in FIG. 1.

On a sheet form substrate 1 made of polyethylene terephthalate (PET), a carbon electrode 2 having a silver lead wire is formed by silk screen printing. On the electrode 2, a PET spacer 3 having a space 3' which receives a test liquid is adhered with a double-coated adhesive tape. On the top surface of the spacer 3 (opposite to the electrode 2), a lid 4 is adhered with a double-coated adhesive tape. The test liquid is supplied in the space 3' from an opening 7, whereby the measurement is carried out.

The substance(s) are placed by one of the following methods (A), (B) and (C):

(A) On an area 5 having a specific surface area of the carbon electrode 2, 3.3 mM potassium ferricyanide (30 $\mu$l) is dropped and dried to place a solid layer of potassium ferricyanide.

(B) On a surface 6 of the lid 7, before the lid is adhered, 0.1M citrate buffer (5 $\mu$l) containing 160 mM potassium ferricyanide and 400 U/ml of lactate oxidase was dropped and dried to place a solid layer of the enzyme and potassium ferricyanide.

(C) On an area 5 having a specific surface area of the carbon electrode 2, 3.3 mM potassium ferricyanide (30 $\mu$l) is dropped and dried to place a solid layer of potassium ferricyanide. Also, on a surface 6 of the lid 7, before the lid is adhered, 0.1M citrate buffer (5 $\mu$l) containing 160 mM potassium ferricyanide and 400 U/ml of lactate oxidase was dropped and dried to place a solid layer of the enzyme and potassium ferricyanide.

EXAMPLE 2

Figure 2:
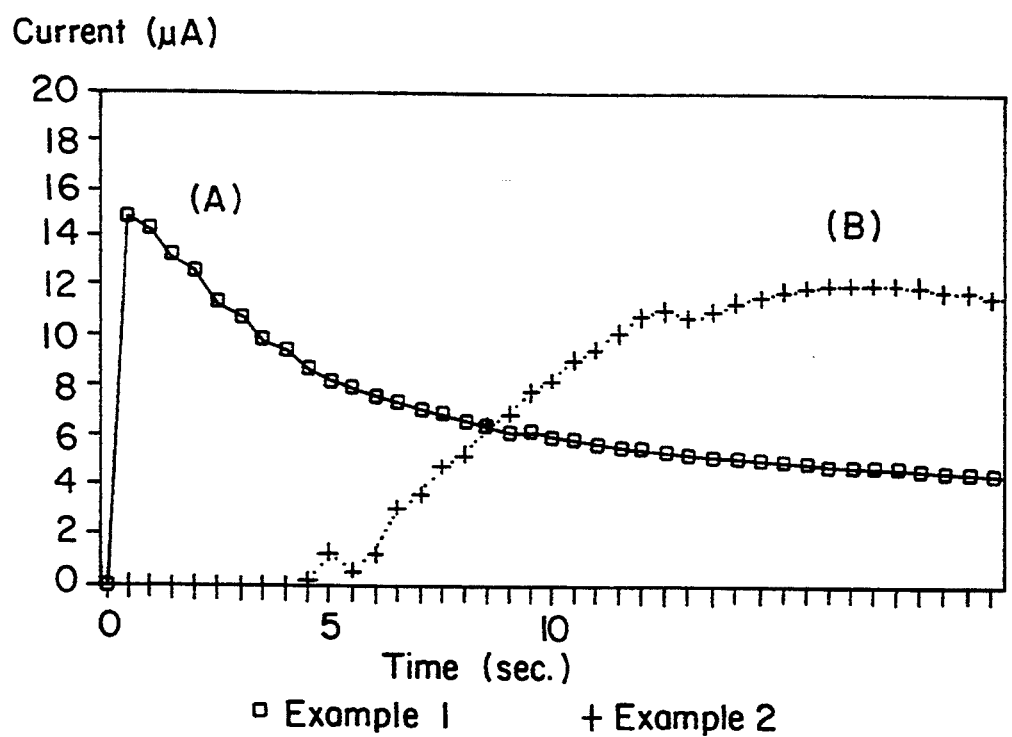
FIG. 2 is a graph showing anodizing currents measured in Examples 1 and 2.

From the opening 7 of the sensor produced by the method (A) in Example 1, 2 mM aqueous solution of ascorbic acid (10 μl) was introduced. Simultaneously, a constant voltage of +200 mV was applied between a detection electrode and a counter electrode and an anodizing current was measured. The result is shown in FIG. 2 (line A). The anode current reached the maximum value after 0.5 second by the application of +200 mV. This means that the reduction reaction of potassium ferricyanide with ascorbic acid is very fast and the current generated by this reaction is detected quickly.

EXAMPLE 3

In the same manner as in Example 2 but using the sensor produced by the method (B) in Example 1 and 5 mM aqueous solution of lactic acid (10 μl), the change of the anodizing current was measured. The result is shown in FIG. 2 (line B). The anode current was substantially 0 μA after 4 seconds from the start of the application of +200 mV. This means that the arrival of potassium ferricyanide generated by the enzymatic reaction of lactic acid at the position 6 of FIG. 1 was delayed by about 4 seconds.

EXAMPLE 4

An aqueous solution was prepared by adding ascorbic acid at a concentration of 0 mg/dl, 17.6 mg/dl or 35.2 mg/dl (each an end concentration) to a solution of lactic acid of a concentration of 0 mg/dl, 9.0 mg/dl, 18.0 mg/dl or 45.0 mg/dl. Then, 10 μl of each of the solutions was introduced in the sensor produced by the method (C) from the opening 7. Simultaneously, a first voltage of +200 mV was applied for 4 seconds between a detection electrode and a counter electrode and an anodizing current was measured. After 30 seconds from the introduction of the test solution, a second voltage of +200 mV was applied for 5 seconds, during which the anodizing current was measured. The result is shown in FIGS. 3 to 5, which show the changes of the anode current with time using the solutions containing 0 mg/dl (FIG. 3), 17.6 mg/dl (FIG. 4) or 35.2 mg/dl (FIG. 5) of ascorbic acid and 9.0 mg/dl, 18.0 mg/dl or 45.0 mg/dl of lactic acid.

Figure 3:
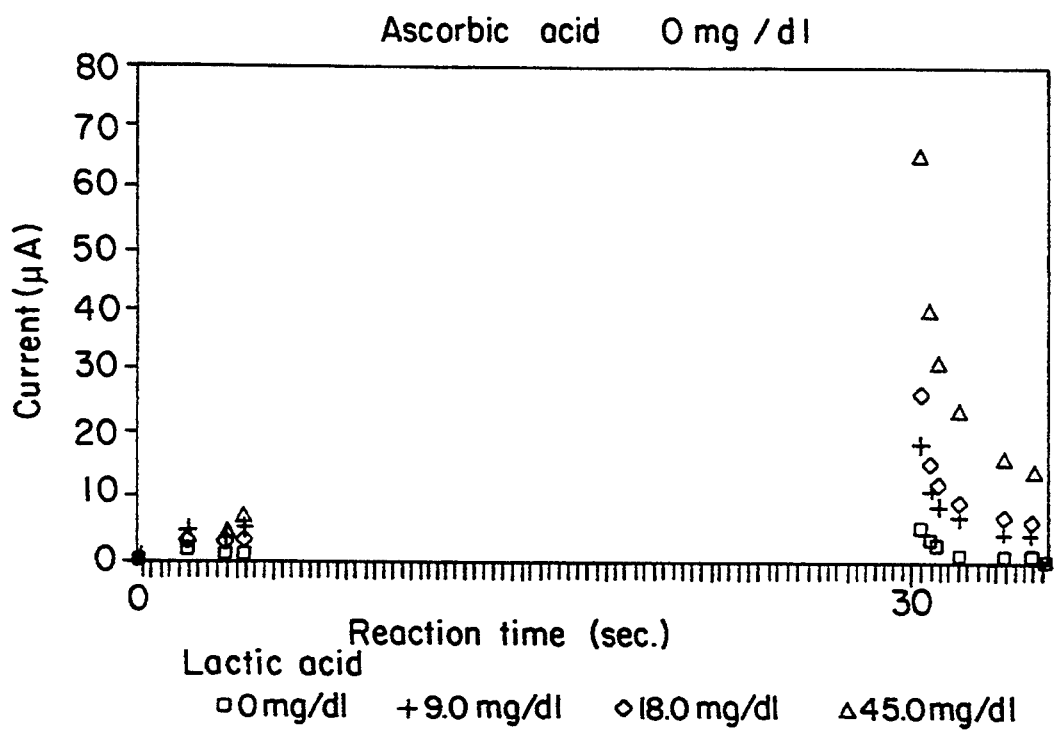
FIGS. 3, 4 and 5 are graphs showing changes of anodizing currents at lactic acid concentrations of 0 mg/dl, 17.6 mg/dl and 35.2 mg/dl, respectively.
Figure 4:
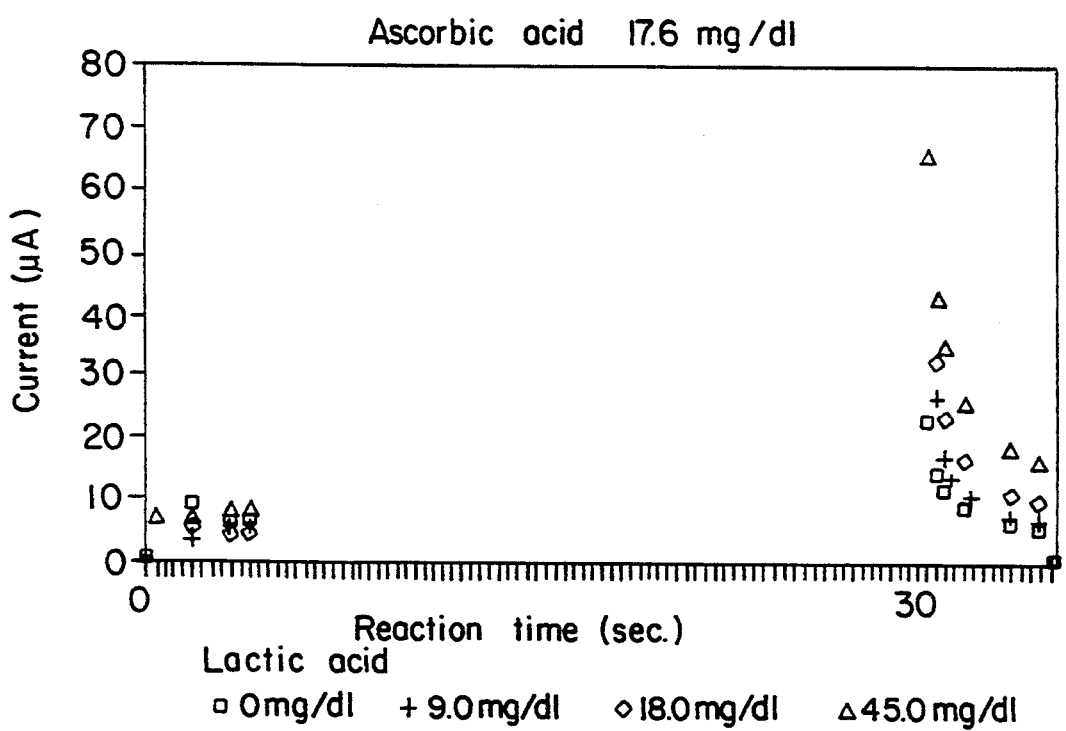
Figure 5:
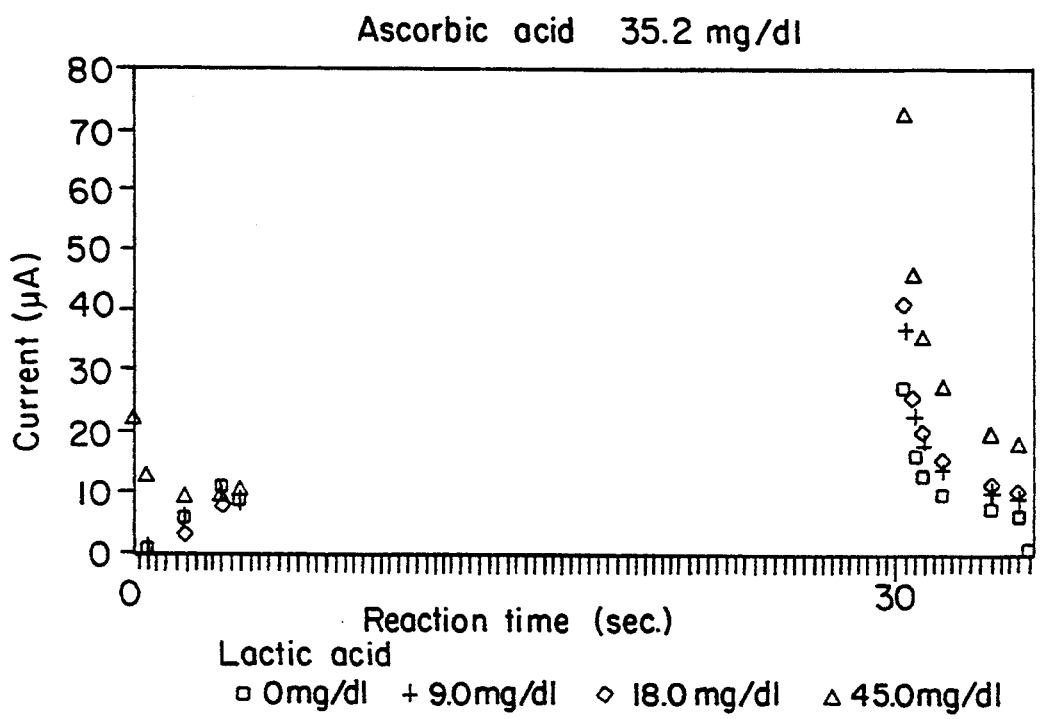
Figure 6:
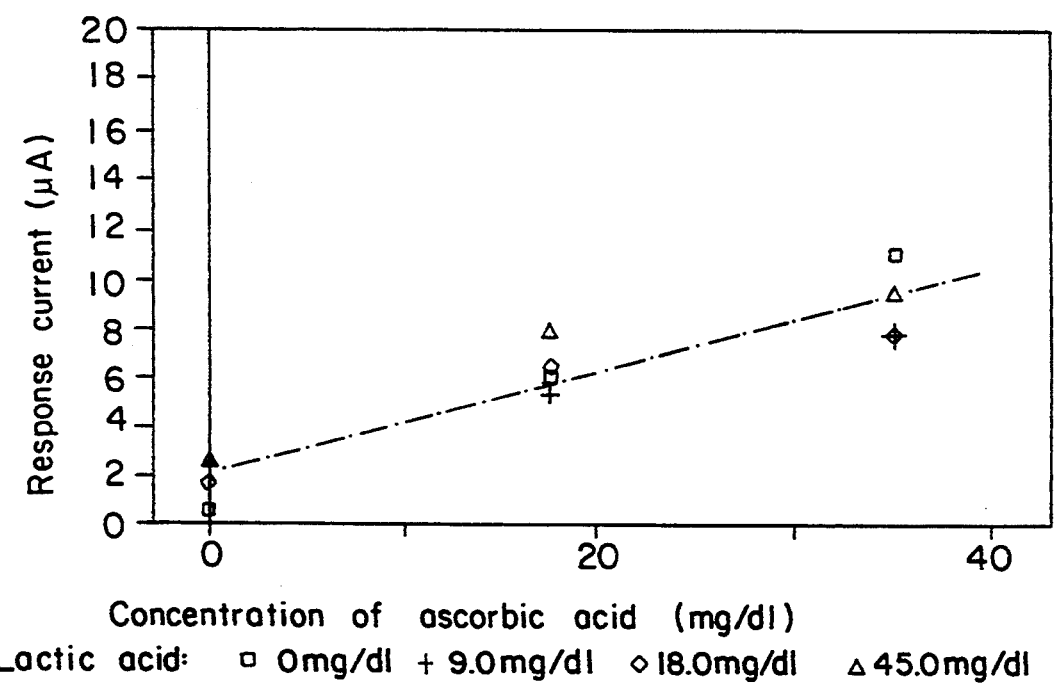
FIG. 6 is a calibration curve of response currents in FIGS. 3, 4 and 5 after 4 seconds from the start of measurement against the concentration of ascorbic acid.

FIG. 6 shows a calibration curve, in which the response currents (anode currents) in FIGS. 3 to 5 after 4 seconds from the introduction of the test solution were on the ordinate and the concentrations of ascorbic acid were on the abscissa. Though the lactic acid concentrations varied widely, the calibration curves for the three different lactic acid concentrations could be approximated by one calibration curve.

Figure 7:
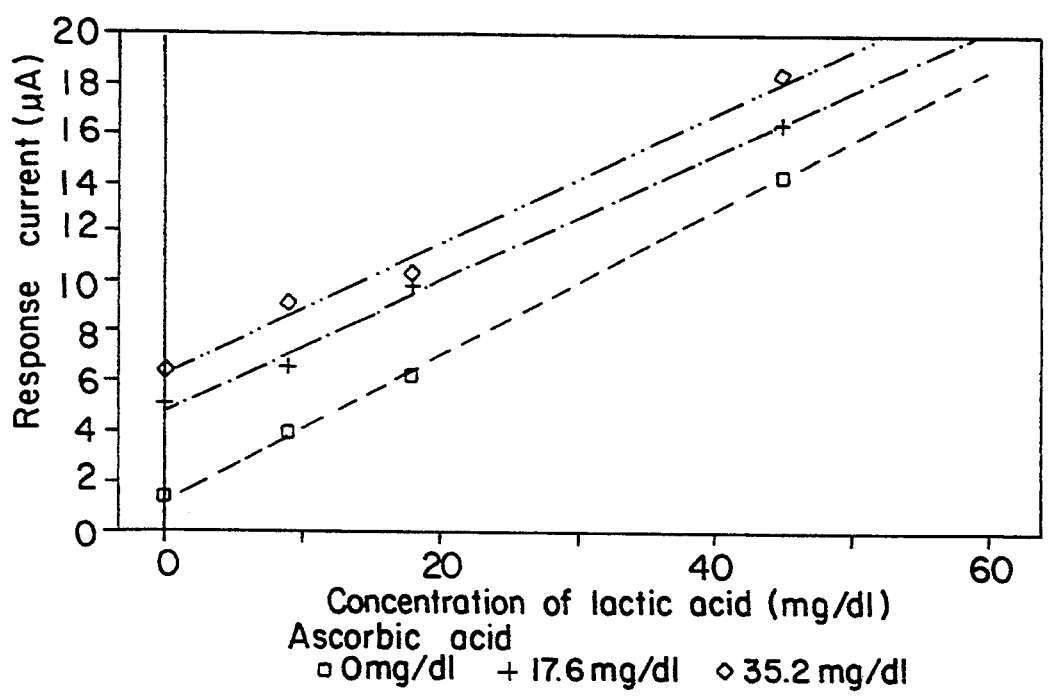
FIG. 7 is a calibration curve of response currents in FIGS. 3, 4 and 5 after 35 seconds from the start of the measurement against the concentration of lactic acid.

FIG. 7 shows calibration curves, in which the response currents (anode currents) in FIGS. 3 to 5 after 35 seconds from the introduction of the test solution were on the ordinate and the concentrations of lactic acid were on the abscissa. The calibration curves shifted in the positive direction of the ordinate with the response current corresponding to the respective concentration of ascorbic acid. This means that ascorbic acid has a positive interference against the measurement of lactic acid.

Figure 8:
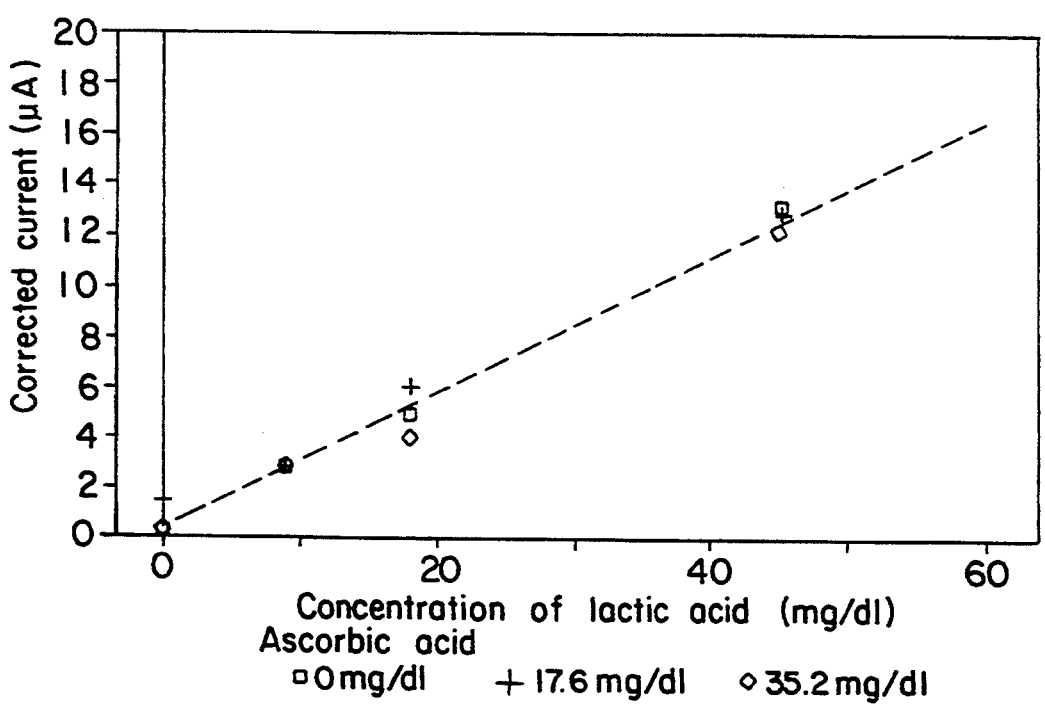
FIG. 8 is a corrected calibration curve obtained by correcting the calibration curve of FIG. 7 with that of FIG. 6.

The calibration curves of FIG. 7 were corrected using the calibration curve of FIG. 6. That is, by taking into consideration the sensitivity difference of the response current between the time of the first voltage application and the time of the second voltage application, the calibration curve of FIG. 6 was corrected so that each of the calibration curves of FIG. 7 corresponding to the ascorbic acid concentration of 0 mg/dl and 35.2 mg/dl passed the origin, and then, using the corrected calibration curve, all the measured values in FIG. 7 were corrected. The results are shown in FIG. 8. In spite of the large difference of the ascorbic acid concentrations, all the calibration curves could be approximated by a single calibration curve. This means that the concentration of lactic acid is separated from that of ascorbic acid. Namely, the interference of ascorbic acid is avoided from the measurement.

What is claimed is:

1. A biosensor which electrochemically detects a material which relates to a reaction of a specific compound in a liquid sample with a biologically active substance, wherein the biologically active material is placed at a part which is remote from a position of an electrode which-acts as electrochemical detector means.

2. The biosensor according to claim 1, which comprises a mediator which is placed at a part which is remote from said position of said electrode together with said biologically active substance.

3. The biosensor according to claim 1, which comprises a mediator which is provided on said electrode.

4. The biosensor according to claim 1, wherein said biologically active substance is bound with a hydrophilic polymer.

5. The biosensor according to claim 3, wherein said mediator is covered with a layer of a hydrophilic polymer.

6. The biosensor according to claim 1, wherein said biologically active substance is an enzyme.

7. The biosensor according to claim 6, wherein said enzyme is an oxidoreductase.

* * * * *